United States Patent
Kondo et al.

(10) Patent No.: US 6,356,775 B1
(45) Date of Patent: Mar. 12, 2002

(54) BIOLOGICAL DATA OBSERVATION SYSTEM

(75) Inventors: Shinji Kondo; Hirohide Urano, both of Kariya (JP)

(73) Assignees: Kyoho Machine Works. Ltd., Totoya; Kabushiki Gaisya K-and S, Kariya, both of (JP)

( * ) Notice: Subject to any disclaimer, the term of this patent is extended or adjusted under 35 U.S.C. 154(b) by 0 days.

(21) Appl. No.: 09/550,208

(22) Filed: Apr. 17, 2000

(30) Foreign Application Priority Data

Apr. 20, 1999 (JP) .......................... 11-112223

(51) Int. Cl.[7] .............................. A61B 5/05
(52) U.S. Cl. ...................... 600/346; 600/306
(58) Field of Search ................. 600/300, 346, 600/306, 547, 345; 128/898

(56) References Cited

U.S. PATENT DOCUMENTS

| | | | |
|---|---|---|---|
| 3,727,604 A | * 4/1973 | Sidwell et al. | 600/547 |
| 4,013,067 A | 3/1977 | Kreese et al. | |
| 4,805,636 A | 2/1989 | Barry et al. | |
| 5,906,208 A | * 5/1999 | Ishikawa et al. | 600/306 |
| 5,917,415 A | * 6/1999 | Atlas | 600/372 |
| 6,233,471 B1 | * 5/2001 | Berner et al. | 600/345 |

FOREIGN PATENT DOCUMENTS

| | | |
|---|---|---|
| EP | 0 149 866 | 7/1985 |
| EP | 0 787 506 | 8/1997 |
| JP | A-8-322823 | 12/1996 |
| JP | A-8322824 | 12/1996 |
| JP | A8-322825 | 12/1996 |
| JP | A-9-271516 | 10/1997 |
| JP | A-11-56785 | 3/1999 |

* cited by examiner

Primary Examiner—John P. Lacyk
Assistant Examiner—Navin Natnithithadha
(74) Attorney, Agent, or Firm—Oblon, Spivak, McClelland, Maier & Neustadt, P.C.

(57) ABSTRACT

A biological data observation system makes it possible to accurately observing the anesthetic depth of a patient. The system measures a signal based on the pulse wave of the patient, and measures the sweat rate. During a surgery, these data and/or their composite data is monitored. The system displays transition of the sweat rate. Therefore, if during the surgery the patient's condition changes, an operating doctor (operator) will immediately notice a change in the sweat rate displayed by the system, so that the doctor or the like can promptly take an appropriate measure for the change in the patient's condition. By observing the transition of the patient's blood pressure displayed by the system, the doctor can also understand how the patient's condition changes as a result of the doctor's measure.

38 Claims, 11 Drawing Sheets

BIOLOGICAL DATA OBSERVATION SYSTEM

INCORPORATION BY REFERENCE

The disclosure of Japanese Patent Application No. HEI 11-112223 filed on Apr. 20, 1999 including the specification, drawings and abstract is incorporated herein by reference in its entirety.

BACKGROUND OF THE INVENTION

1. Field of the Invention

The present invention relates to a biological data observation system that monitors the anesthetic depth of a patient.

2. Description of the Related Art

To anesthetize a patient during a surgery, an anesthetic gas is continuously supplied to, for example, a mask placed over the patient's mouth. If the amount of the anesthetic gas supplied is excessively small, the anesthetic depth of the patient becomes insufficient, so that the patient feels pains during the surgery. Conversely, if the anesthetic depth of a patient is excessive, the patient may fall into narcosis. Therefore, in the conventional biological data observation systems, the blood pressure of a patient is measured and displayed on a monitor. While referring to a blood pressure transition curve displayed on the monitor, an anesthesiologist adjusts the anesthetic dosage.

In general, the biological data related to movements or conditions of a heart, such as blood pressure and the like, responds to administration of an anesthetic with a delay. Therefore, monitoring only the transition of blood pressure of a patient poses a danger of a delay in coping with a change in the patient's condition or a change in the patient's anesthetic depth. Furthermore, the blood pressure hardly change (the change is very little) in response to a stimulus given to a patient even if the patient feels a pain. Therefore, with a system that measures only blood pressure transition, it is difficult to monitor the degree of a pain that a patient feels.

SUMMARY OF THE INVENTION

Accordingly, it is an object of the invention to provide a biological data observation system capable of observing the anesthetic depth of a patient with an increased accuracy.

To achieve the aforementioned and other objects, the invention provides a biological data observation system for monitoring an anesthetic depth of a patient, the system including a first measuring device that measures a first biological data based on an amount of perspiration of the patient. The system also includes a data processor that substantially continuously receives the data measured by the first measuring device, and that determines a transition of the data, and an indicator that externally indicates the transition of the data determined by the data processor.

Perspiration or sweating is generally divided into emotional sweating and thermal sweating. The emotional sweating is known to be greatly affected by the autonomic nervous system. In the description below, the emotional sweating and the thermal sweating are collectively referred to as "perspiration" or "sweating". In a condition where autonomic nerves are inhibited, such as an anesthetized condition or the like, the amount of perspiration or the sweat rate is less than that in a normal condition (where the autonomic nerves are not inhibited), and increases upon a stimulus. In general, such an emotional sweat rate change is caused by control of autonomic nerve control prior to a subjective symptom. That is, perspiration is governed by autonomic nerves, and the sweat rate of a patient sensitively changes in relation to a stimulus applied to the patient, the anesthetic depth of the patient, or the like. Therefore, the system of the invention makes it possible to detect a sign of a change in the anesthetic depth based on transition of the sweat rate. Furthermore, when a stimulus is applied to an anesthetized patient in order to observe a response of the patient, the system makes it possible to observe a pain felt by the patient in terms of the sweat rate, which is quantitative data.

Thus, since the system of the invention measures the sweat rate of a patient as well as the patient's pulse wave, the system makes it possible to more accurately observe the anesthetic depth of a patient during a surgery.

Further, by measuring transition of the patient's pulse wave (blood pressure or the like), the system also makes it possible to observe movements or conditions of the patient's heart in relation to an anesthetic agent.

BRIEF DESCRIPTION OF THE DRAWINGS

The foregoing and further objects, features and advantages of the present invention will become apparent from the following description of preferred embodiments with reference to the accompanying drawings, wherein like numerals are used to represent like elements and wherein.

DETAILED DESCRIPTION OF PREFERRED EMBODIMENTS

Preferred embodiments of the invention will be described hereinafter with reference to the accompanying drawings.

A first embodiment of the invention will be described with reference to FIGS. 1 to 8.

Figure 1:
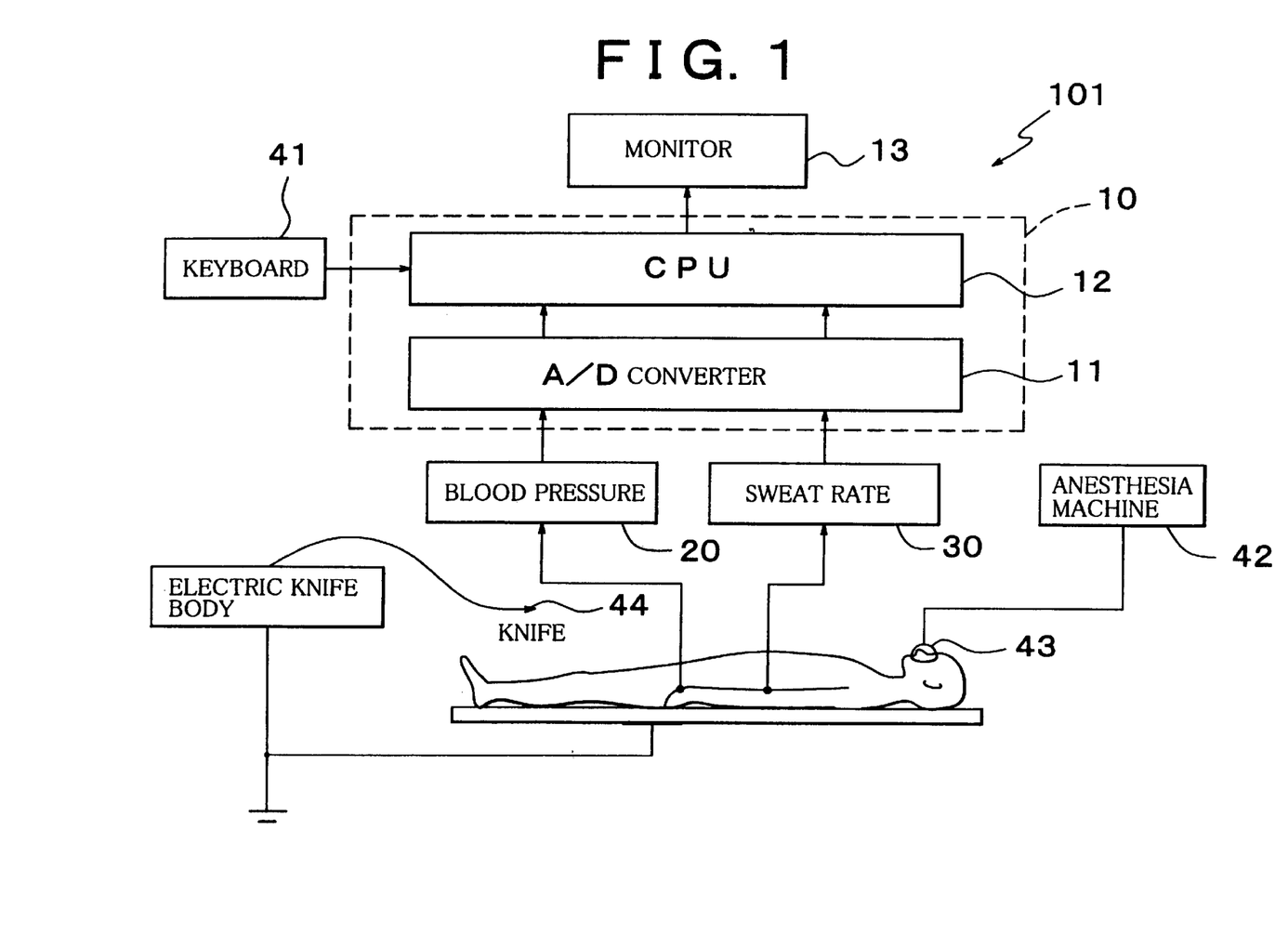
FIG. 1 is a block diagram of a biological data observation system according to a first embodiment of the invention.

As shown in FIG. 1, in a biological data observation system 101, output lines of a blood pressure measuring device 20 and a sweat rate measuring device 30 are connected to a data processing device 10.

Figure 2:
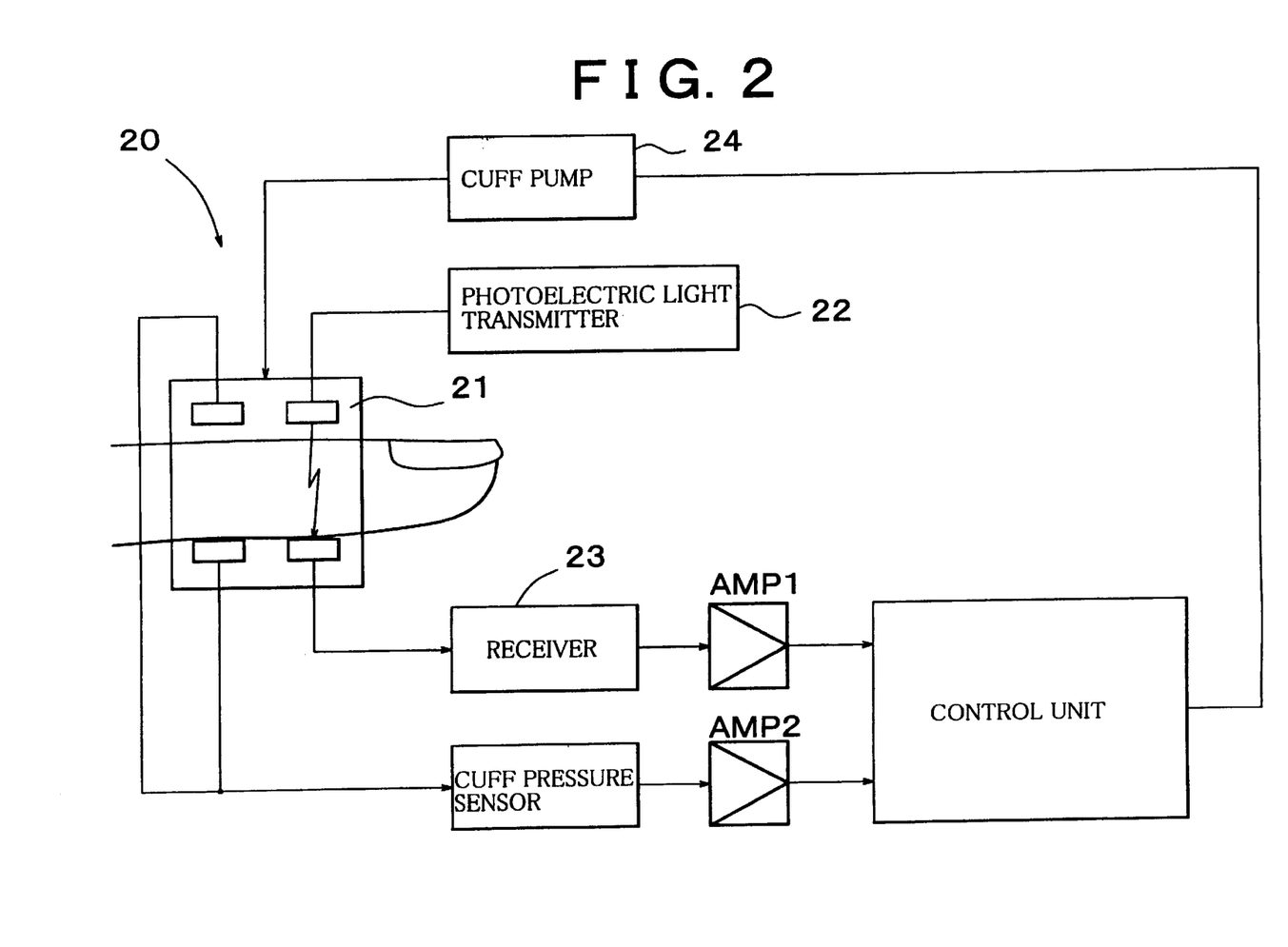
FIG. 2 is a block diagram of a blood pressure measuring device.

A construction of the blood pressure measuring device 20 is illustrated in FIG. 2. The blood pressure measuring device 20 measures the blood pressure of a patient through calculation of the patient's pulse wave (heart beats, pulses) based on a predetermined converting equation according to a generally-termed blood pressure waveform continuous measurement method. Specifically, an air-filled cuff band 21 is placed around a finger of the patient. While a photoelectrical capacity pulse wave is detected by using a photoelectric light transmitter 22 and a photoelectric light receiver 23 that are disposed at opposite sides of the patient's finger, the cuff pressure is adjusted to balance with the intravascular pressure by controlling the output of a cuff pump 24. In this condition, the blood pressure waveform is continuously measured, and is outputted as a blood pressure signal (for example, an analog signal).

Figure 3:
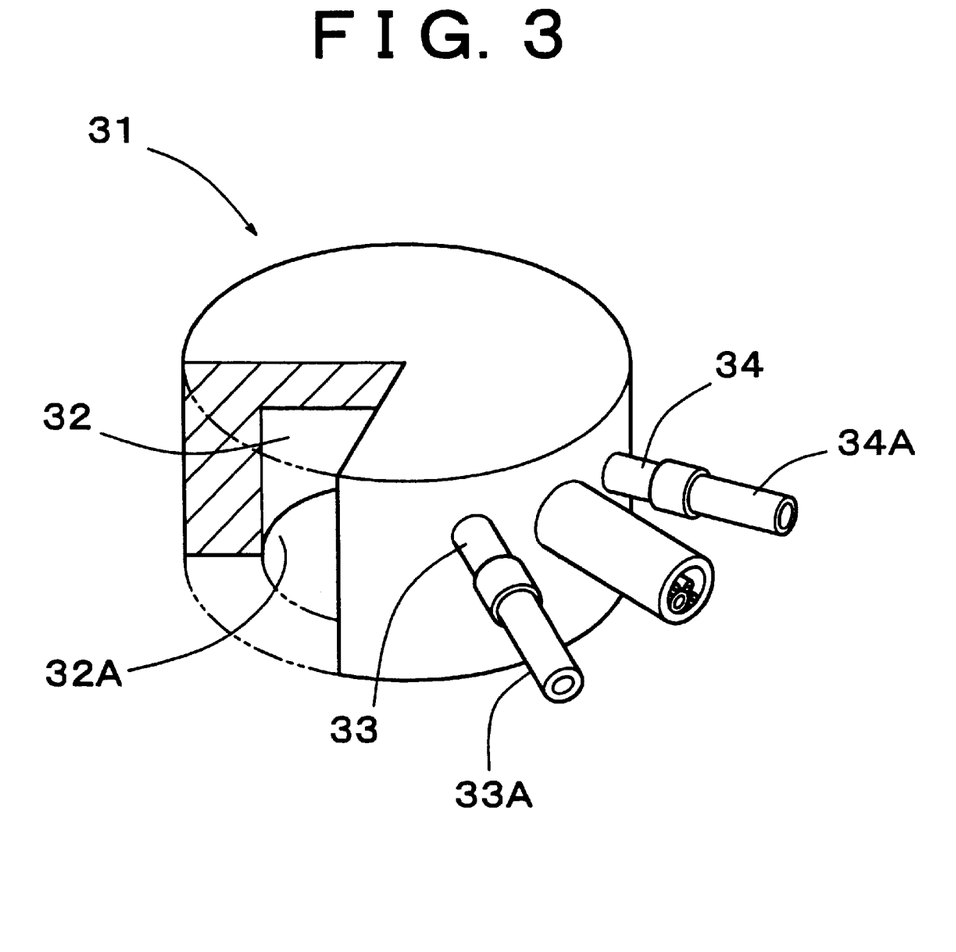
FIG. 3 is a partially cutaway perspective view of a capsule of a sweat rate detecting device.

As shown in FIG. 3, the sweat rate measuring device 30 is provided with a capsule 31. The capsule 31 is attached to the patient so that an opening 32A of a recess 32 formed in the capsule 31 is closed by a skin surface of the patient. A peripheral surface of the capsule 31 is provided with a supply opening 33 and a discharge opening 34 that communicate with the recess 32. The recess 32 is supplied with, for example, a low-humidity nitrogen gas at a constant flow rate, from a tank (not shown) via the supply opening 33 and a rubber tube 33A connected thereto. A hygrometer (not shown) is provided in partway of a rubber tube 34A connected to the discharge opening 34, thereby measuring the humidity of discharged air. A thermometer and a heater/cooler (e.g., a Peltier device) are provided in the capsule 31. The heater/cooler is controlled so as to maintain a constant temperature in the recess 32. Based on outputs from the hygrometer and the thermometer, the absolute humidity is detected. The detected absolute humidity is outputted as an analog signal (sweat rate signal).

Figure 4:
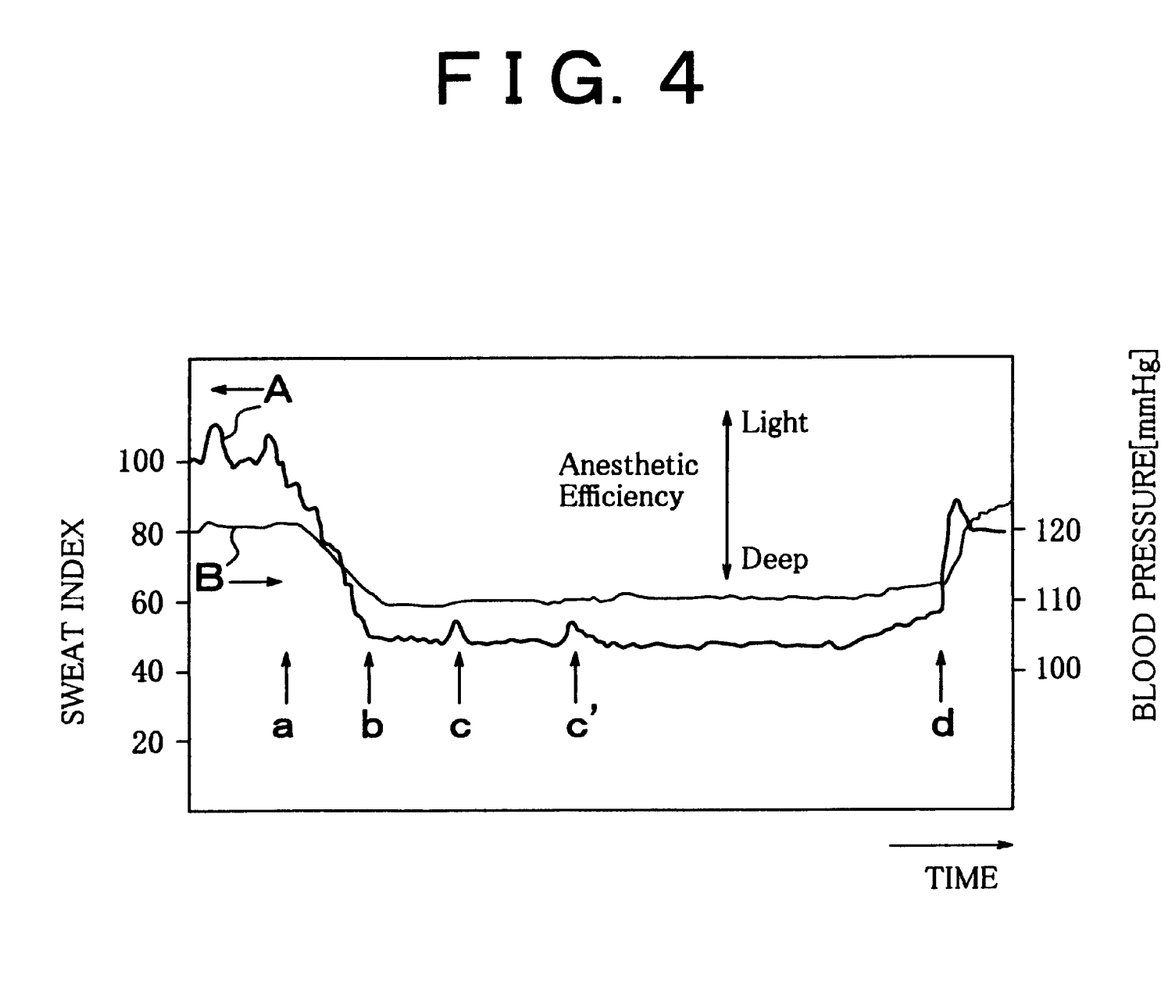
FIG. 4 is a graph indicating transitions of blood pressure data and sweat rate data.

FIG. 4 indicates transitions of blood pressure data (Line A) and sweat rate data (Line B).

When an anesthetic gas is supplied to a patient (at the point a in FIG. 4), the sweat rate decreases. The blood pressure also decrease, but responds to administration of an anesthetic with a delay. The amount of the anesthetic gas is increased up to a predetermined amount, and then becomes a steady state where the amount of the supplied gas is constant. After that (point b in FIG. 4), the sweat rate become stable. If the anesthetic depth is insufficient (light), the sweat rate sensitively changes when a stimulus is applied to the patient (points c and c' in FIG. 4). Because the sweat rate sensitively changes according to "pain" which is one of stimulus autonomic nerves. Meanwhile the blood pressure does not change at the points c and c' in FIG. 4. Therefore, it is possible to monitor the anesthetic depth of the patient by measuring the sweat rate. After a surgery (point d in FIG. 4), the sweat rate increase because the patient comes out from the anesthetic. Since this invention measures the sweat rate of the patient during the surgery, it is possible to determine that the patient has come out from the anesthetic when the sweat rate reaches the sweat rate which has been memorized at the beginning of the surgery.

Figure 5:
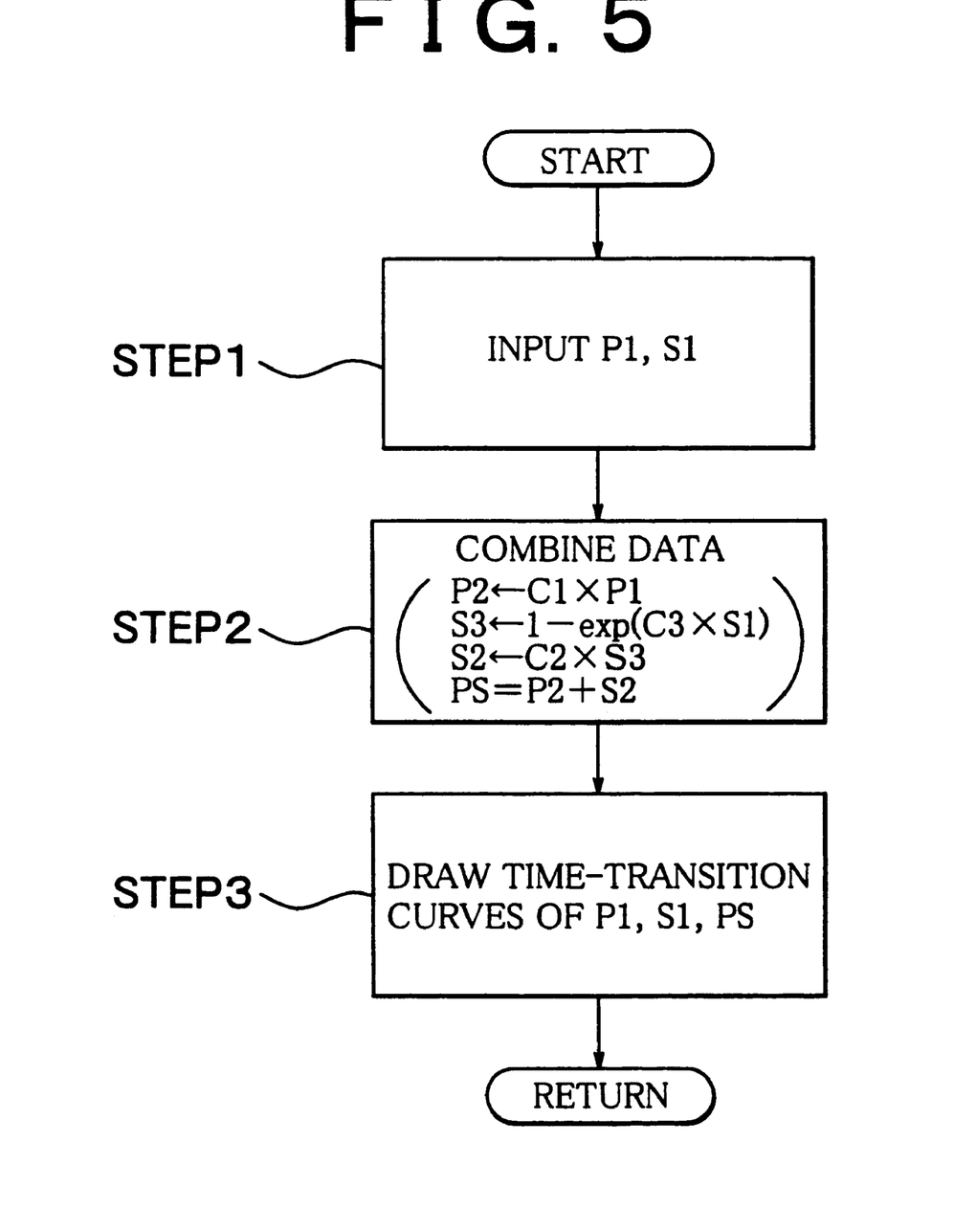
FIG. 5 is a flowchart illustrating a procedure of combining a blood pressure signal and a sweat rate signal.

The data processing device 10 has an A/D converter 11, and thereby converts the blood pressure signal and the sweat rate signal into digital signals, and inputs them into ports of a CPU 12. Upon power-up, the CPU 12 loads a program from a ROM (not shown) provided in the data processing device 10. In this embodiment, CPU 12 also executes data processing as illustrated in the flowchart of FIG. 5 to calculate blood pressure data P1, sweat rate data S1, and composite data PS (described in detail below) so that perform more precise evaluation of the anesthetic depth.

Figure 8:
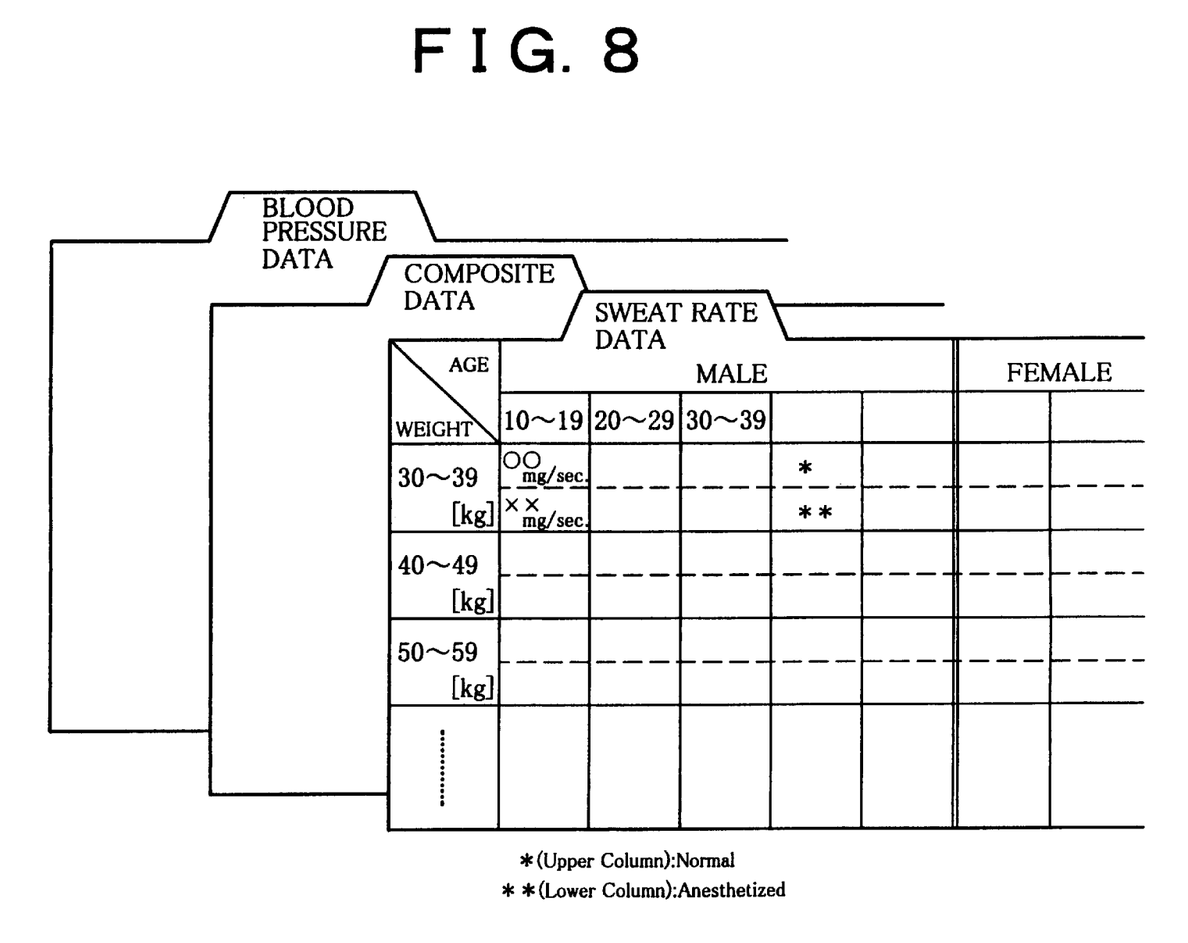
FIG. 8 is a conceptual diagram of data tables stored in a ROM.

Blood pressure data P1, sweat rate data S1 and composite data obtained during an anesthetized condition and a normal condition are pre-stored in the ROM in the data processing device 10, as standard data, with parameters of, for example, age, sex, body weight and the like. The standard data is prepared beforehand by, for example, an experienced anesthesiologist actually collecting blood pressure data, sweat rate data and composite data at the time of administration of an anesthetic to patients, and aggregating or summarizing the collected data. The standard data is provided in the form of data tables as indicated in FIG. 8.

The data processing device 10 is connected to a monitor 13 (e.g., CRT) for externally displaying contents of measurement and processing.

A biological data observing method according to this embodiment will be described in detail with reference to FIG. 5.

Before administration of an anesthetic to a patient, the system 101 is set on the patient. More specifically, the cuff band 21 of the blood pressure measuring device 20 and the capsule 31 of the sweat rate measuring device 30 are attached to the patient's body, and then the data processing device 10, the blood pressure measuring device 20 and the sweat rate measuring device 30 are powered on. Subsequently, the patient's age, sex and body weight are inputted to the data processing device 10 from a keyboard 41.

When the biological data observation system 101 is activated, the blood pressure signal from the blood pressure measuring device 20 and the sweat rate signal from the sweat rate measuring device 30 are converted into digital signals by the A/D converter 11, and then are inputted to the data processing device 10. In accordance with the program loaded upon the power-up, the CPU 12 writes the input blood pressure signal and the input sweat rate signal as a variable P1 and a variable S1 into predetermined memory areas (STEP 1 in FIG. 5). Hereinafter, these data are referred to as "blood pressure data P1" and "sweat rate data S1" for easier description.

Next, the CPU 12 combines the blood pressure data P1 and the sweat rate data S1 (STEP 2 in FIG. 5). In this embodiment, composite data PS is calculated as in equations (1) to (4).

$$P2 = C1 \times P1 \tag{1}$$

$$S2 = C2 \times S3 \tag{2}$$

$$S3 = 1 - \exp(C3 \times S1) \tag{3}$$

$$PS = P2 + S2 \tag{4}$$

where C1 and C2 are positive constants, and C3 is a negative constant (C1>0, C2>0, C3<0).

Figure 6:
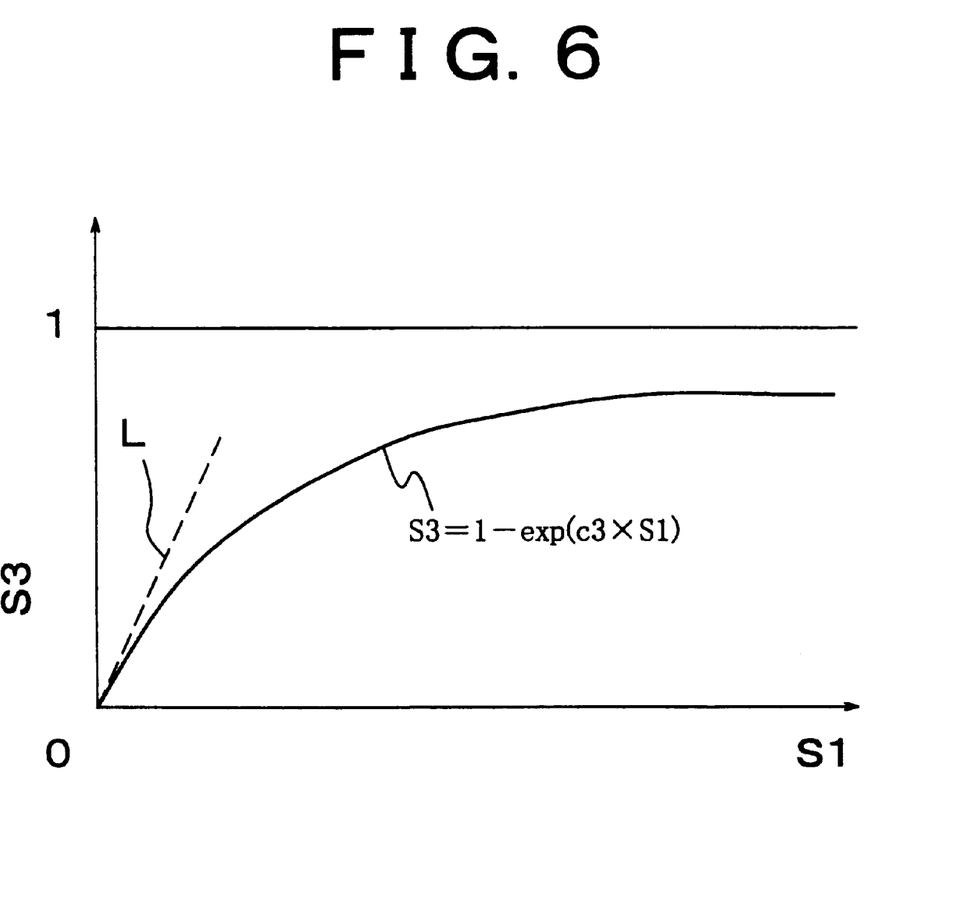
FIG. 6 is a graph for illustrating an intermediate step of data processing.

The relationship between the sweat rate data S1 and the value S3 determined by equation (3) is indicated in FIG. 6.

Figure 7A:
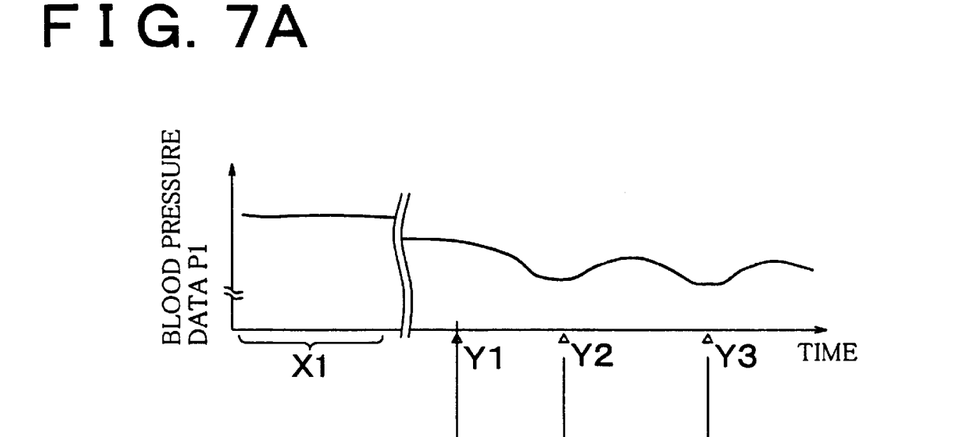
FIG. 7A is a graph indicating transition of blood pressure data.
Figure 7B:
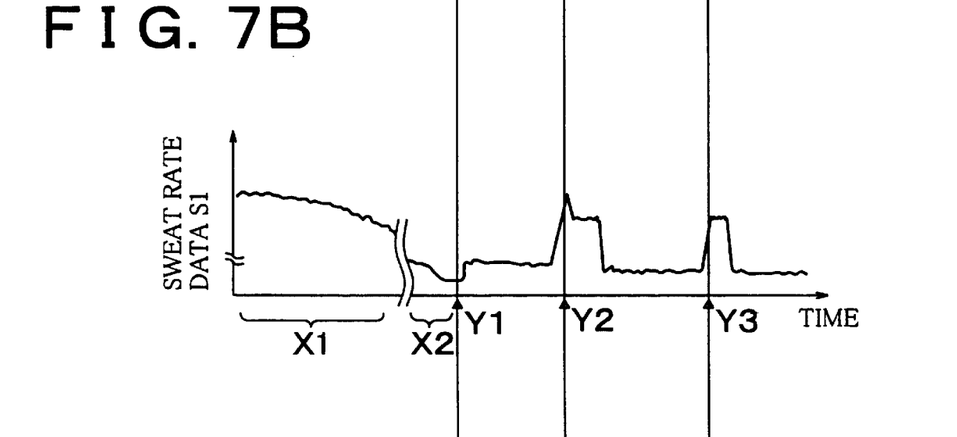
FIG. 7B is a graph indicating transition of sweat rate data.
Figure 7C:
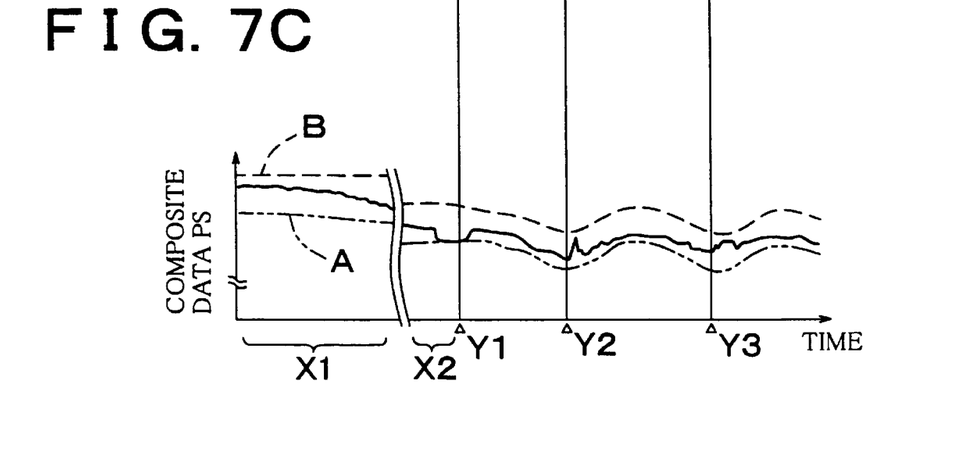
FIG. 7C is a graph indicating transition of composite data based on the blood pressure data and the sweat rate data.

After calculating the composite data PS, the CPU. 12 causes the monitor 13 connected to the data processing device 10 to draw time-transition curves of the blood pressure data P1, the sweat rate data S1 and the composite data PS (STEP 3 in FIG. 5). Examples of displayed transition curves of the blood pressure data P1, the sweat rate data S1 and the composite data PS are shown in FIGS. 7A, 7B and 7C, respectively. If necessary, it is possible to display on the monitor 13 personal data (age, body weights and the like) inputted to the data processing device 10 from the keyboard 41, and the standard data of blood pressure data P1 and sweat rate data S1 and composite data PS for the normal condition and the anesthetized condition (stored in the ROM of the data processing device 10) based on the personal data, as well as transition curves as shown in FIGS. 7A to 7C.

After the transition curves displayed on the monitor 13 become stable, the blood pressure data P1, the sweat rate data S1 and the composite data PS are all compared with the standard data. In this embodiment, it is assumed that the data of the patient accords with (conforms to) the standard data. If an actual measurement greatly differs from the standard data due to individual patient difference, the difference between the actual measurement and the standard data is inputted to the data processing device 10 by using the keyboard 41. The difference may be displayed as a correction value on the monitor 13.

After that, the mask 43 connected to an anesthesia machine 42 is attached to the patient, and then the anesthesia machine 42 is activated. Then, an anesthetic gas is supplied via the mask 43, so that the anesthetic enters the patient's blood via the respiratory system. When the anesthetic in blood reaches the patient's brain, the brain sends a signal to autonomic nerves so that the sweat rate decreases. In response, the humidity in the recess 32 of the capsule 31 decreases. Therefore, the transition curves of the sweat rate data S1 and the composite data PS exhibit rightward decreasing tendencies as indicated in stage X1 in FIGS. 7B and 7C. In this stage, however, the blood pressure transition curve normally remains horizontal (exhibits substantially no change) as shown in FIG. 7A since the blood pressure delays in responding to the anesthetic administration.

As the anesthetic depth increases with increases in the uptake of the anesthetic into the patient's body, the sweat rate data S1 and the composite data PS become quite low as indicated in a stage X2 in FIGS. 7B and 7C.

If the amount of the anesthetic supplied becomes excessive, the sweat rate data S1 becomes lower than the standard data. In that case, the transition curves of the sweat rate data S1 and the composite data PS change as indicated at a time point Y1 in FIGS. 7B and 7C. Therefore, a sign of a change in the patient's condition can be detected.

In this embodiment, the value S3 is determined from the sweat rate data S1 by the exponential function as in equation (3). The value S3 changes corresponding to the sweat rate data S1 as indicated in FIG. 6. That is, the value S3 sharply rises in a range where the sweat rate data S1 is relatively small. Therefore, small changes occurring in the range of relatively small sweat rate data S1 can be reflected in the value S3. Since the value S3 is loaded on the blood pressure data PI in equation (4) to generate the composite data PS, small changes in the sweat rate (FIG. 7B) are also displayed as changes in the composite data PS on the monitor 13 as shown in FIG. 7C. The degree of rising of the curve of S3 in FIG. 6 (the gradient of a broken line L in FIG. 6) can be adjusted by changing the value of constant C3 in equation (3).

The value S3 changes as indicated in FIG. 6, and does not exceed 1 regardless of how much the sweat rate increases. Furthermore, since the value S3 is loaded on the blood pressure data P1 to generate the composite data PS, the composite data PS changes between the transition curve of the blood pressure (two-dot chain line A in FIG. 7C) and a curve (a chain line B in FIG. 7C) offset from the blood pressure transition curve. Therefore, even if the sweat rate greatly changes, the transition of the blood pressure is reflected as overall changes in the transition curve of the composite data PS.

The blood pressure data P1, the sweat rate data S1 and the composite data PS of the patient become stable and substantially equal to the standard data prepared for the anesthetized condition, a stimulus (e.g., an electric stimulus) is applied to the patient. For example, if electric stimuli are given at time points Y2, Y3 in FIGS. 7A to 7C, the sweat rate data S1 and the composite data PS change as indicated in FIGS. 7B and 7C. Thus, this embodiment makes it possible to observe pains of the patient quantitatively based on the sweat rate. If the sweat rate data S1 becomes excessively large, it is considered that the patient feels a pain, and then the amount of anesthetic supplied is slightly increased. Therefore, the embodiment makes it possible to relatively precisely and easily observe the condition of a patient, in comparison with observation based on facial features of a patient.

After the anesthetic depth becomes stable, the surgery is started (for example, a body area concerned is cut by an electric knife 44). In the system 101 of this embodiment, by observing the composite data PS displayed on the monitor 13, an operating doctor or the like can simultaneously observe for a sign of a change in the anesthetic depth based on the transition of the sweat rate and can observe the anesthetic depth based on the transition of the blood pressure, at a glance. Therefore, the burden on operating doctors during a surgery decreases. If the sweat rate becomes out of a predetermined range, a doctor will realize a change in the patient's condition during the surgery, merely by observing changes in the sweat rate displayed on the monitor 13. Therefore, the doctor or the like can promptly take an appropriate measure. After that, the doctor or the like can understand how the patient's condition changes as a result of the measure, by observing the transition of the blood pressure displayed on the monitor 13.

In this embodiment, it is also possible to display only the transition curve of the composite data PS on the monitor 13.

Figure 9:
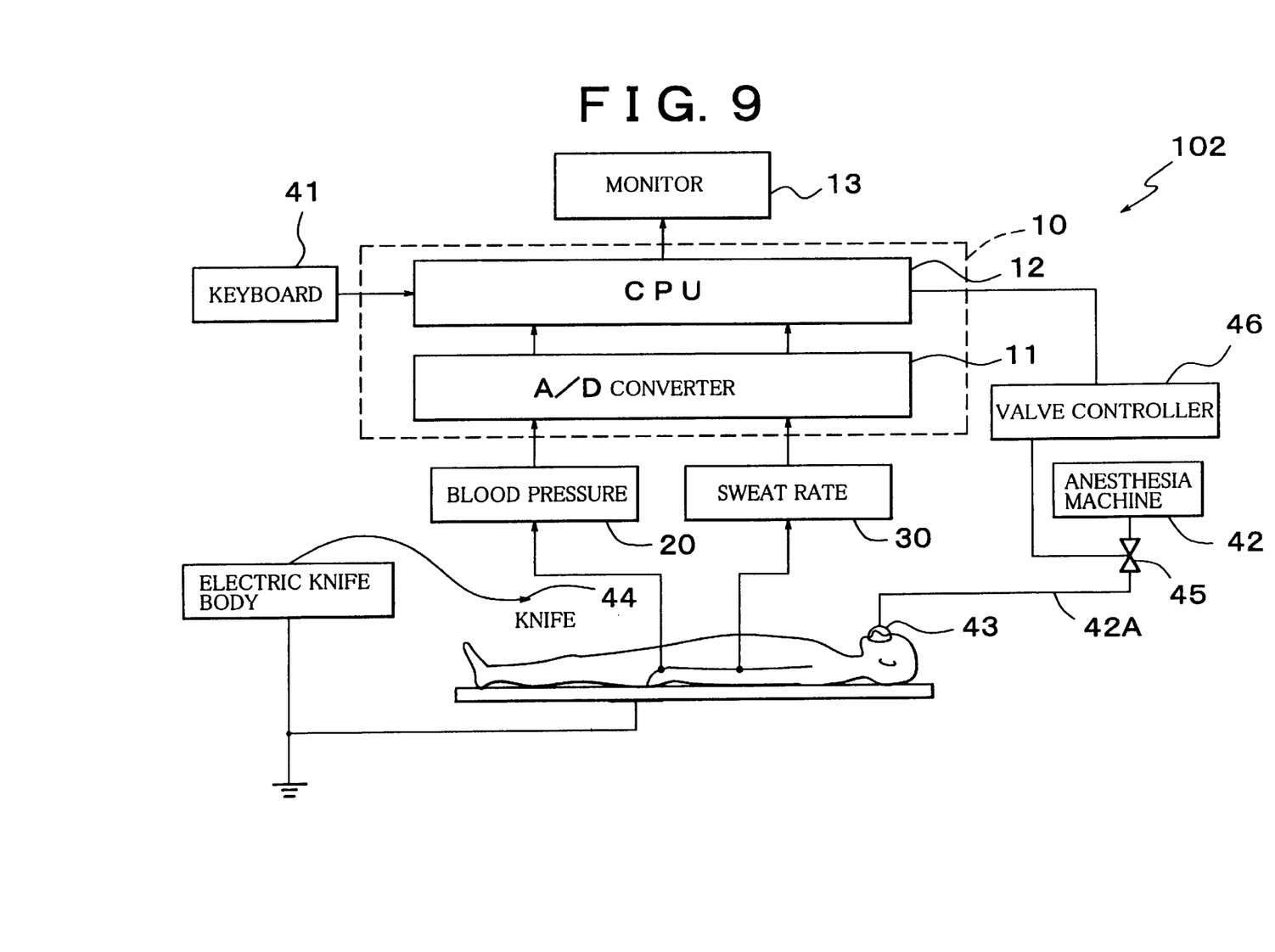
FIG. 9 is a block diagram of a biological data observation system according to a second embodiment of the invention.

A second embodiment of the biological data observation system of the invention will be described with reference to FIG. 9. Only constructions that distinguish the second embodiment from the first embodiment will be described.

In a biological data observation system 102 of the second embodiment, an electromagnetic valve 45 for adjusting the flow of an anesthetic gas is provided in partway of an anesthetic gas supplying line 42A extending between an anesthesia machine 42 and a mask 43. The electromagnetic valve 45 is driven by a valve drive circuit 46. The valve drive circuit 46 adjusts the extent of opening of the electromagnetic valve 45 based on an instruction from a CPU 12.

In this embodiment, the control of the system 102 is switched to an automatic mode, for example, when the anesthetic depth becomes stable and the surgery is to be started. The supply of an anesthetic is increased (or decreased), for example, if both the blood pressure data P1 and the sweat rate data S1 become abnormally large (or small), i.e., become out of predetermined ranges, that is, if the composite data PS becomes abnormally large (or small), i.e., becomes out of a predetermined range. Thus, the supply of the anesthetic gas can be automatically adjusted to a predetermined amount, so that the anesthetic depth of a patient can be kept in a stable state and the burden on an operating doctor can be reduced.

In this embodiment, the amount of supply of the anesthetic is changed based on changes in the composite data in order to perform the control with an increased precision. However, it is also possible to change the amount of supply of the anesthetic when one of the blood pressure data and the sweat rate data exhibits an abnormal change.

Figure 10:
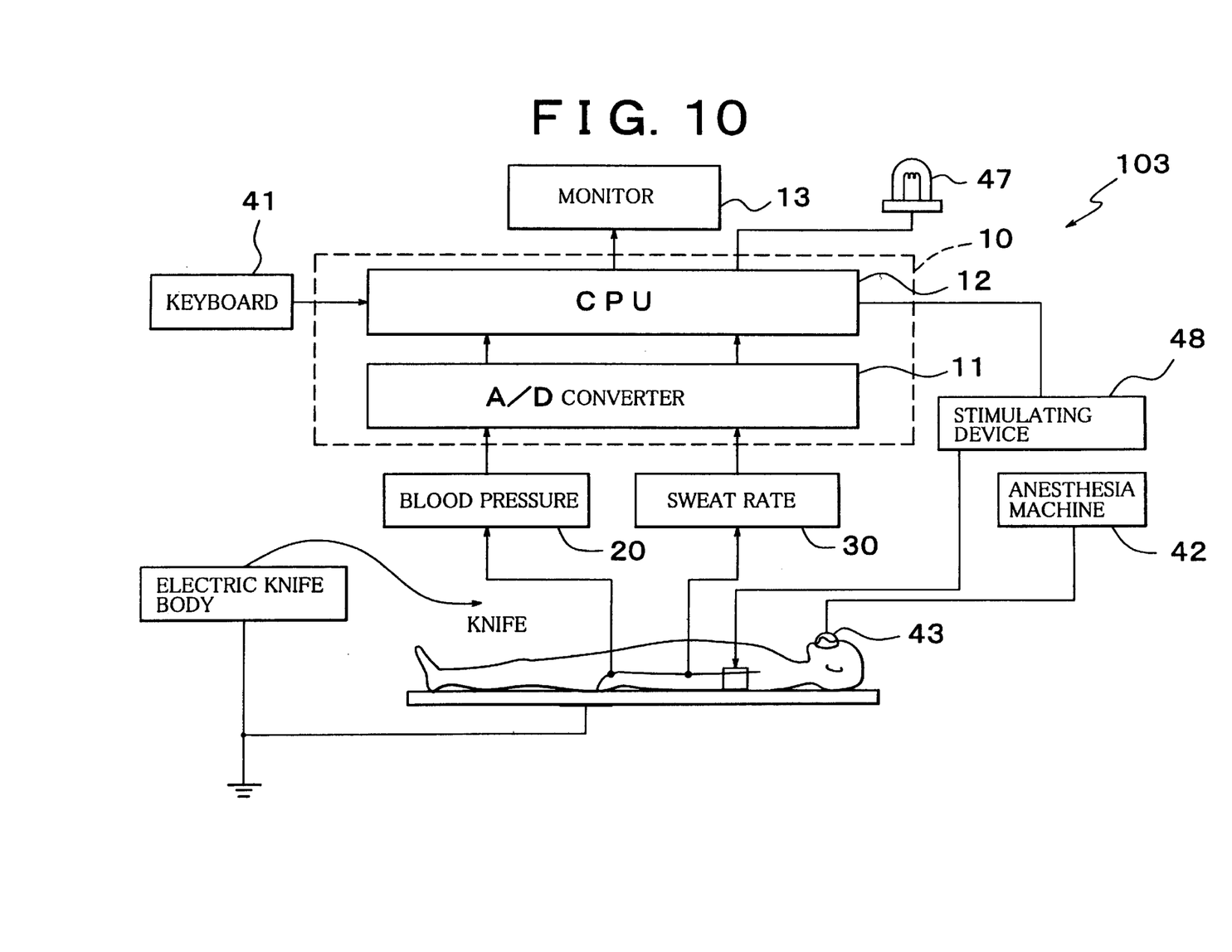
FIG. 10 is a block diagram of a biological data observation system according to a third embodiment of the invention.

A third embodiment of the biological data observation system of the invention will be described with reference to FIG. 10. Constructions that distinguish the third embodiment from the first embodiment will be described below.

In a biological data observation system 103 of the third embodiment, a warning light 47 and a simulating device 48 are connected to a data processing device 10. A CPU 12 provided in the data processing device 10 turns on the data processing device 10 and the simulating device 48 when the composite data PS assumes an abnormal value. When the simulating device 48 applies an electric current stimulus to the patient, responses to the stimulus are detected by a blood pressure measuring device 20 and a sweat rate measuring device 30. If the composite data PS does not increase in response to the electric current stimulus, it can be determined that the anesthetic depth is excessively great. Therefore, more precise evaluation of the anesthetic depth becomes possible. Furthermore, the turning-on of the warning light 47 calls attention of the doctors and nurses. Therefore, a sudden change in the patient's condition can be promptly coped with.

In this embodiment, the warning light 47 and the simulating device 48 may be activated when one of the blood pressure data P1 and the sweat rate data S1 assumes an abnormal value, instead of the composite data PS assuming an abnormal value.

Figure 11:
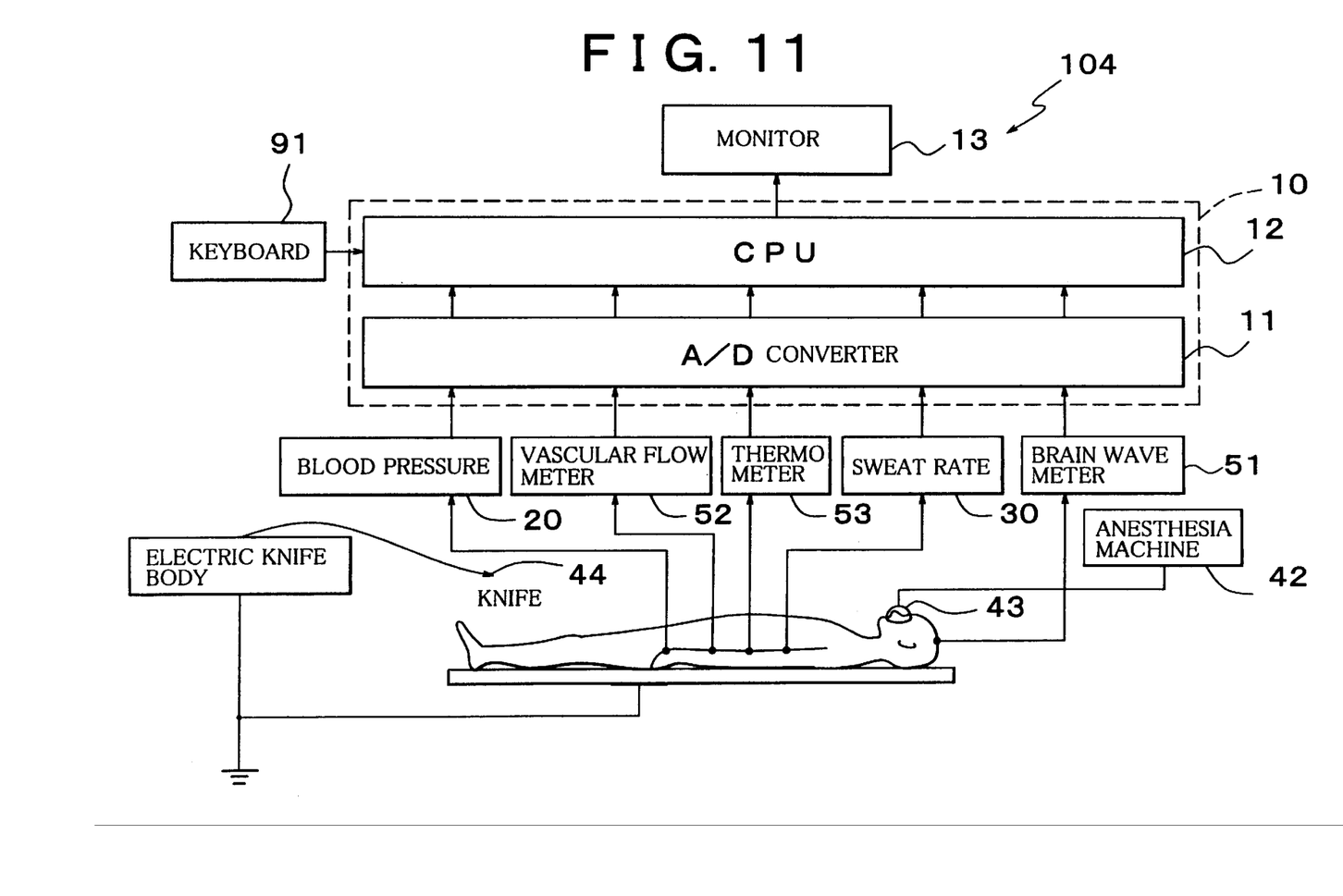
FIG. 11 is a block diagram of a biological data observation system according to a fourth embodiment of the invention.

A fourth embodiment of the biological data observation system of the invention will be described with reference to FIG. 11. Constructions that distinguish the fourth embodiment from the first embodiment will be described below.

In a biological data observation system 104 of the fourth embodiment, a brain wave sensor 51, a vascular flow sensor 52 and a body temperature senor 53 are connected to a data processing device 10. When at least one (e.g., three) of the data from these sensors, the blood pressure data P1, the sweat rate data S1 and the composite data PS assumes an abnormal value, it is determined that a change in the patient's condition has occurred. By referring to increased number of kinds of data, changes in the patient's condition can be more accurately observed. Furthermore, when the system 104 determines abnormal data, it is also possible to produce, for example, a warning sound from the data processing device.

Although in the foregoing embodiments, an anesthetic agent is supplied in the form of an anesthetic gas, the invention is also applicable to a case where an anesthetic agent is administered by drip infusion or the like.

Furthermore, although in the foregoing embodiments, measured data regarding the pulse wave is converted into a blood pressure signal before being inputted to the data processing device 10, measured data regarding the pulse wave may also be directly inputted and subjected to data processing.

While the present invention has been described with reference to what are presently considered to be preferred embodiments thereof, it is to be understood that the present invention is not limited to the disclosed embodiments or constructions. On the contrary, the present invention is intended to cover various modifications and equivalent arrangements.

What is claimed is:

1. A biological data observation system for monitoring an anesthetic depth of a patient, comprising:
    a first measuring device that measures a first biological data based on an amount of perspiration of the patient;
    a data processor that substantially continuously receives the data measured by the first measuring device and that determines a transition of the data; and
    an indicator that externally indicates the transition of the data determined by the data processor.

2. A system according to claim 1, further comprising a second measuring device that measures a second biological data based on a pulse wave of the patient, wherein the data processor substantially continuously receives the data measured by the second measuring device and that determines a transition of the data.

3. A system according to claim 2, wherein the second biological data is heart beats.

4. A system according to claim 2, wherein the second biological data is a blood pressure.

5. A system according to claim 2, wherein the data processor calculates a third biological data based on the first biological data and the second biological data.

6. A system according to claim 5, wherein the second biological data is a blood pressure.

7. A system according to claim 5, further comprising an anesthesia device that is capable of substantially continuously administering an anesthetic agent to the patient, wherein the data processor calculates a third biological data based on the first biological data and the second biological data, and adjusts an amount of the anesthetic agent administered by the anesthesia device, based on the third biological data calculated.

8. A system according to claim 7, wherein the second biological data is a blood pressure.

9. A system according to claim 7, further comprising a warning device that outputs a warning signal when at least one of the first biological data, the second biological data and the third biological data becomes out of a predetermined range.

10. A system according to claim 9, wherein the second biological data is a blood pressure.

11. A system according to claim 9, further comprising an electric current stimulator that gives an electric current stimulus to the patient when at least one of the first biological data, the second biological data and the third biological data becomes out of the predetermined range.

12. A system according to claim 11, wherein the second biological data is a blood pressure.

13. A system according to claim 7, further comprising an electric current stimulator that gives an electric current stimulus to the patient when at least one of the first biological data, the second biological data and the third biological data becomes out of a predetermined range.

14. A system according to claim 13, wherein the second biological data is a blood pressure.

15. A system according to claim 5, further comprising a warning device that outputs a warning signal when at least one of the first biological data, the second biological data and the third biological data becomes out of a predetermined range.

16. A system according to claim 15, wherein the second biological data is a blood pressure.

17. A system according to claim 15, further comprising an electric current stimulator that gives an electric current stimulus to the patient when at least one of the first biological data, the second biological data and the third biological data becomes out of the predetermined range.

18. A system according to claim 17, wherein the second biological data is a blood pressure.

19. A system according to claim 5, further comprising an electric current stimulator that gives an electric current stimulus to the patient when at least one of the first biological data, the second biological data and the third biological data becomes out of a predetermined range.

20. A system according to claim 19, wherein the second biological data is a blood pressure.

21. A system according to claim 2, further comprising an anesthesia device that is capable of substantially continuously administering an anesthetic agent to the patient, wherein the data processor calculates a third biological data based on the first biological data and the second biological data, and adjusts an amount of the anesthetic agent administered by the anesthesia device, based on the third biological data calculated.

22. A system according to claim 21, wherein the second biological data is a blood pressure.

23. A system according to claim 21, further comprising a warning device that outputs a warning signal when at least one of the first biological data, the second biological data and the third biological data becomes out of a predetermined range.

24. A system according to claim 23, wherein the second biological data is a blood pressure.

25. A system according to claim 24, further comprising an electric current stimulator that gives an electric current stimulus to the patient when at least one of the first biological data, the second biological data and the third biological data becomes out of the predetermined range.

26. A system according to claim 25, wherein the second biological data is a blood pressure.

27. A system according to claim 21, further comprising an electric current stimulator that gives an electric current stimulus to the patient when at least one of the first biological data, the second biological data and the third biological data becomes out of a predetermined range.

28. A system according to claim 27, wherein the second biological data is a blood pressure.

29. A system according to claim 2, further comprising a warning device that outputs a warning signal when at least one of the first biological data and the second biological data becomes out of a predetermined range.

30. A system according to claim 29, wherein the second biological data is a blood pressure.

31. A system according to claim 29, further comprising an electric current stimulator that gives an electric current stimulus to the patient when at least one of the first biological data and the second biological data becomes out of the predetermined range.

32. A system according to claim 31, wherein the second biological data is a blood pressure.

33. A system according to claim 2, further comprising an electric current stimulator that gives an electric current stimulus to the patient when at least one of the first biological data and the second biological data becomes out of a predetermined range.

34. A system according to claim 33, wherein the second biological data is a blood pressure.

35. A system according to claim 2, wherein the indicator is a display.

36. A system according to claim 1, wherein the first measuring device measures an absolute humidity on a surface of the patient as an amount of perspiration of the patient.

37. A system according to claim 36, further comprising a container, that is set on the surface of the patient to enclose an area from the atmosphere, wherein the first measuring device measures th e absolute humidity from the area.

38. A system according to claim 37, further comprising a humidity meter that measures a humidity of the enclosed area, and a temperature meter that measures a temperature of the enclosed area, wherein the first measuring device measures the absolute humidity based on the humidity measured by the humidity meter and the temperature measure d by the temperature meter.

* * * * *